United States Patent
Peters et al.

(10) Patent No.: US 9,032,787 B2
(45) Date of Patent: May 19, 2015

(54) METHOD AND SYSTEM FOR MAGNETIC PARTICLE DETECTION IN A CHARGE AIR SYSTEM

(71) Applicant: General Electric Company, Schenectady, NY (US)

(72) Inventors: Eric David Peters, Lawrence Park, PA (US); Larry Gene Anderson, Lawrence Park, PA (US); Roshan Shekhar Kotian, Lawrence Park, PA (US); Chirag Bipinchandra Parikh, Lawrence Park, PA (US)

(73) Assignee: General Electric Company, Schenectady, NY (US)

( * ) Notice: Subject to any disclaimer, the term of this patent is extended or adjusted under 35 U.S.C. 154(b) by 259 days.

(21) Appl. No.: 13/770,073

(22) Filed: Feb. 19, 2013

(65) Prior Publication Data

US 2014/0230407 A1  Aug. 21, 2014

(51) Int. Cl.
*G01M 15/04* (2006.01)
*F01N 11/00* (2006.01)

(52) U.S. Cl.
CPC ..................................... *F01N 11/00* (2013.01)

(58) Field of Classification Search
USPC ............................................ 73/114.01, 114.77
See application file for complete search history.

(56) References Cited

U.S. PATENT DOCUMENTS

| | | | | |
|---|---|---|---|---|
| 4,176,545 | A * | 12/1979 | Oddo | 73/53.07 |
| 4,613,815 | A * | 9/1986 | Christel, Jr. | 324/233 |
| 5,214,377 | A * | 5/1993 | Maurice et al. | 324/204 |
| 5,604,441 | A | 2/1997 | Freese et al. | |
| 5,811,664 | A * | 9/1998 | Whittington et al. | 73/53.07 |
| 6,348,087 | B1 * | 2/2002 | Aslin | 96/210 |
| 6,445,177 | B1 | 9/2002 | Higgins | |
| 6,851,413 | B1 | 2/2005 | Tamol et al. | |
| 7,288,139 | B1 * | 10/2007 | Showalter | 96/1 |
| 2013/0000376 | A1 * | 1/2013 | Allam | 73/1.02 |

* cited by examiner

*Primary Examiner* — Freddie Kirkland, III
(74) *Attorney, Agent, or Firm* — GE Global Patent Operation; John A. Kramer

(57) ABSTRACT

Various methods and systems are provided for detecting particles generated from engine component degradation within an engine system. In one embodiment, a method for an engine comprises indicating engine degradation in response to a buildup of particles in a magnetic field, the magnetic field positioned in a flow of gas.

20 Claims, 7 Drawing Sheets

METHOD AND SYSTEM FOR MAGNETIC PARTICLE DETECTION IN A CHARGE AIR SYSTEM

FIELD

Embodiments of the subject matter disclosed herein relate to an engine, engine components, and an engine system, for example.

BACKGROUND

Engine components may degrade over time, resulting in internally generated wear debris. Wear debris particles may pass through an exhaust system of the engine and exit the engine through a muffler or exhaust stack. Engines may utilize recirculation of exhaust gas from the engine exhaust system to an intake system, a process referred to as exhaust gas recirculation (EGR), to reduce regulated emissions. If the engine uses EGR, a portion of the exhaust carrying wear debris may be cooled and mixed with the charge air in the intake system to be used in the combustion process. When recirculated, internally generated debris may pass through the rest of the engine system, thereby leading to further degradation of engine components.

BRIEF DESCRIPTION

In one embodiment, a method (e.g., a method for controlling an engine system) comprises applying a magnetic field within a gas flow passage through which a gas flow passes, the gas flow including at least some exhaust gas, and measuring a signal produced by particles in the gas flow interacting with the magnetic field.

In this way, metallic wear debris generated within the engine system may be detected by the magnetic field, thereby indicating degradation of engine components.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of methods and systems for detecting particles generated from engine component degradation within an engine system. Degraded engine components may result in wear debris, e.g., small magnetic particles. These particles may travel through the engine system and be present in a flow of exhaust gas. By applying a magnetic field within a gas flow passage which includes at least some exhaust gas, metallic wear particles may be attracted to the magnetic field. A detection circuit may then be used to measure a signal produced by one or more particles in the gas flow interacting with the magnetic field. For example, the signal may comprise establishment of, and/or fluctuations in, an electrical current in a gap between two electrodes or other conductors, due to the particles being present in the gap because of the magnetic field. In this way, the presence of wear particles may be detected and used to determine engine degradation.

The magnetic field used to attract wear particles may be produced by different configurations of magnetic probes and/or electrodes. These probes and electrodes may then be electrically connected to a detection circuit which communicates with an engine control unit. Additionally, the particle detector units may be positioned in different locations in an exhaust gas recirculation system and engine intake system. Further details on the structure, function, and positioning of these particle detectors are discussed further below with reference to FIGS. 2-9.

The approach described herein may be employed in a variety of engine types, and a variety of engine-driven systems. Some of these systems may be stationary, while others may be on semi-mobile or mobile platforms. Semi-mobile platforms may be relocated between operational periods, such as mounted on flatbed trailers. Mobile platforms include self-propelled vehicles. Such vehicles can include on-road transportation vehicles, as well as mining equipment, marine vessels, rail vehicles, and other off-highway vehicles (OHV). For clarity of illustration, a locomotive is provided as an example of a mobile platform supporting a system incorporating an embodiment of the invention.

Figure 1:
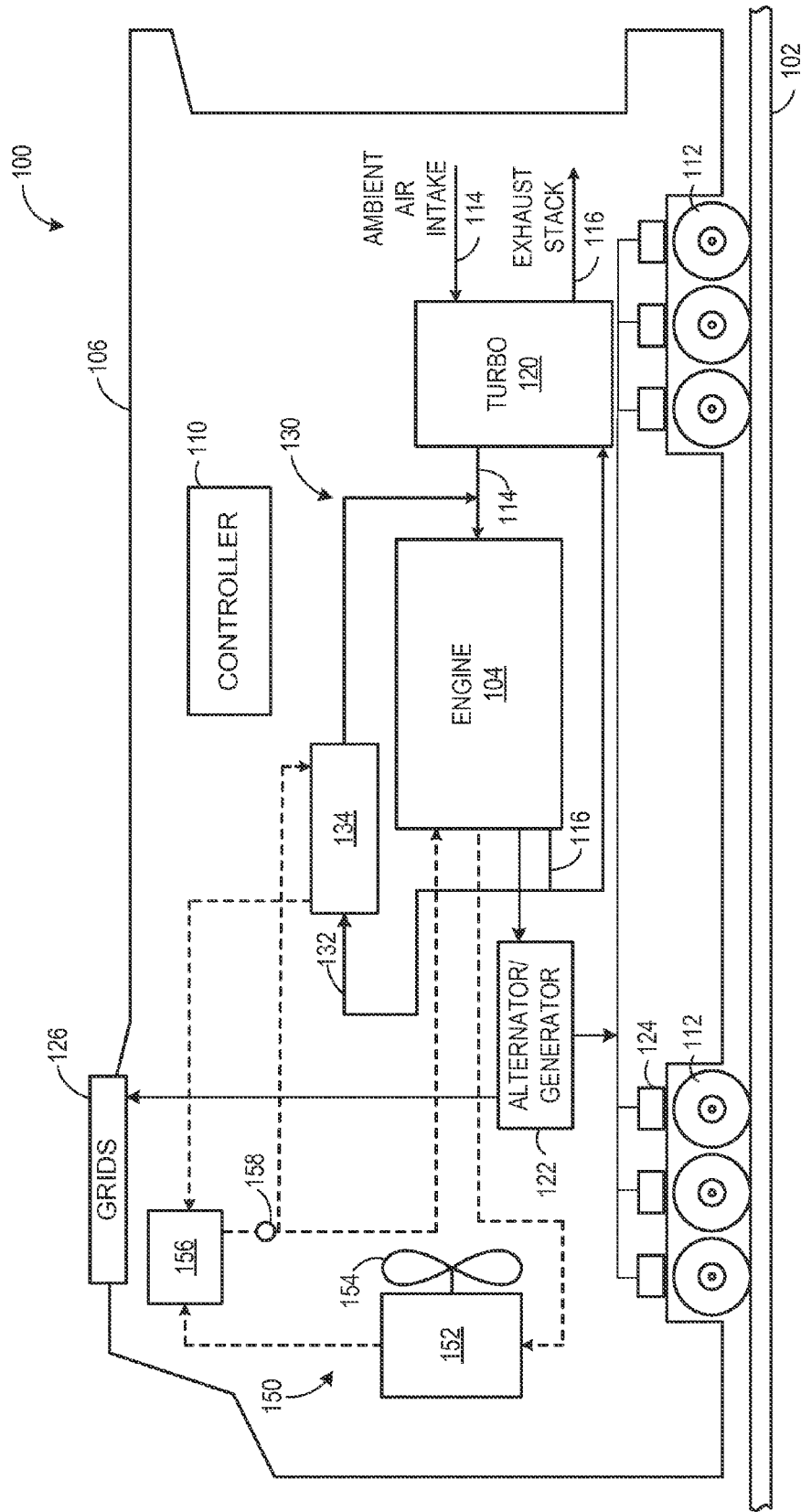
FIG. 1 shows a schematic diagram of an embodiment of a rail vehicle with an engine.

Before further discussion of the approach for detecting wear particles within an engine system, an example of a platform is disclosed in which an engine cylinder bank and EGR system may be configured for an engine in a vehicle, such as a rail vehicle. For example, FIG. 1 shows a block diagram of an example embodiment of a vehicle system 100, herein depicted as a rail vehicle 106 (e.g., locomotive), configured to run on a rail 102 via a plurality of wheels 112. As depicted, the rail vehicle 106 includes an engine 104. In other non-limiting embodiments, the engine 104 may be a stationary engine, such as in a power-plant application, or an engine in a marine vessel or other off-highway vehicle propulsion system as noted above.

The engine 104 receives intake air for combustion from an intake passage 114. The intake passage 114 receives ambient air from an air filter (not shown) that filters air from outside of the rail vehicle 106. Exhaust gas resulting from combustion in the engine 104 is supplied to an exhaust passage 116. Exhaust gas flows through the exhaust passage 116, and out of an exhaust stack of the rail vehicle 106. In one example, the engine 104 is a diesel engine that combusts air and diesel fuel through compression ignition. In other non-limiting embodiments, the engine 104 may combust fuel including gasoline, kerosene, natural gas, biodiesel, or other petroleum distillates of similar density through compression ignition (and/or spark ignition).

In one embodiment, the rail vehicle 106 is a diesel-electric vehicle. As depicted in FIG. 1, the engine 104 is coupled to an electric power generation system, which includes an alternator/generator 122 and electric traction motors 124. For example, the engine 104 is a diesel engine that generates a torque output that is transmitted to the generator 122 which is mechanically coupled to the engine 104. The generator 122 produces electrical power that may be stored and applied for subsequent propagation to a variety of downstream electrical components. As an example, the generator 122 may be electrically coupled to a plurality of traction motors 124 and the generator 122 may provide electrical power to the plurality of traction motors 124. As depicted, the plurality of traction motors 124 are each connected to one of a plurality of wheels 112 to provide tractive power to propel the rail vehicle 106. One example configuration includes one traction motor per wheel. As depicted herein, six pairs of traction motors correspond to each of six pairs of motive wheels of the rail vehicle. In another example, alternator/generator 122 may be coupled to one or more resistive grids 126. The resistive grids 126 may be configured to dissipate excess engine torque via heat produced by the grids from electricity generated by alternator/generator 122.

The vehicle system 100 includes a turbocharger 120 that is arranged between the intake passage 114 and the exhaust passage 116. The turbocharger 120 increases air charge of ambient air drawn into the intake passage 114 in order to provide greater charge density during combustion to increase power output and/or engine-operating efficiency. The turbocharger 120 may include a compressor (not shown) which is at least partially driven by a turbine (not shown). While in this case a single turbocharger is included, the system may include multiple turbine and/or compressor stages.

In some embodiments, the vehicle system 100 may further include an aftertreatment system coupled in the exhaust passage upstream and/or downstream of the turbocharger 120. In one embodiment, the aftertreatment system may include a diesel oxidation catalyst (DOC) and a diesel particulate filter (DPF). In other embodiments, the aftertreatment system may additionally or alternatively include one or more emission control devices. Such emission control devices may include a selective catalytic reduction (SCR) catalyst, three-way catalyst, $NO_x$ trap, or various other devices or systems.

Figure 2:
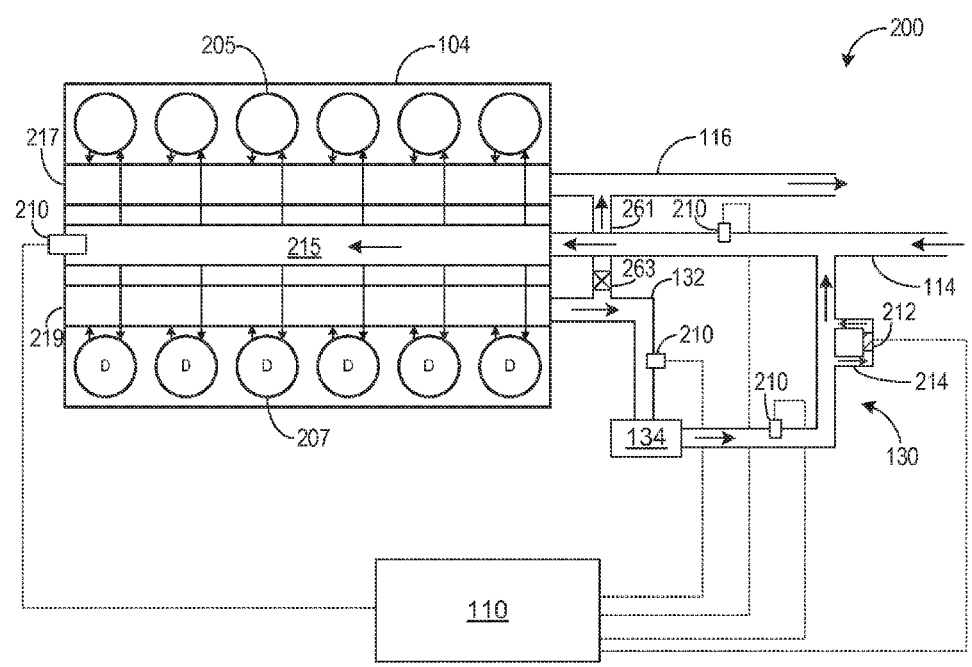
FIG. 2 shows positions of a magnetic particle detector within an engine system according to an embodiment of the invention.

The vehicle system 100 further includes an exhaust gas recirculation (EGR) system 130 coupled to the engine 104, which routes exhaust gas from an exhaust passage 116 of the engine 104 to the intake passage 114 downstream of the turbocharger 120. In some embodiments, the exhaust gas recirculation system 130 may be coupled exclusively to a group of one or more donor cylinders of the engine, as shown in FIG. 2 (discussed further below). As depicted in FIG. 1, the EGR system 130 includes an EGR passage 132 and an EGR cooler 134 to reduce the temperature of the exhaust gas before it enters the intake passage 114. By introducing exhaust gas to the engine 104, the amount of available oxygen for combustion is decreased, thereby reducing the combustion flame temperatures and reducing the formation of nitrogen oxides (e.g., $NO_x$).

In some embodiments, the EGR system 130 may further include an EGR valve for controlling an amount of exhaust gas that is recirculated from the exhaust passage 116 of the engine 104 to the intake passage 114 of engine 104. The EGR valve may be an on/off valve controlled by the controller 110, or it may control a variable amount of EGR, for example. As shown in the non-limiting example embodiment of FIG. 1, the EGR system 130 is a high-pressure EGR system. In other embodiments, the vehicle system 100 may additionally or alternatively include a low-pressure EGR system, routing EGR from downstream of the turbine to upstream of the compressor.

As depicted in FIG. 1, the vehicle system 100 further includes a cooling system 150. The cooling system 150 circulates coolant through the engine 104 to absorb waste engine heat and distribute the heated coolant to a heat exchanger, such as a radiator 152. A fan 154 may be coupled to the radiator 152 in order to maintain an airflow through the radiator 152 when the vehicle 106 is moving slowly or stopped while the engine is running. In some examples, fan speed may be controlled by a controller.

Coolant which is cooled by the radiator 152 enters a tank 156. The coolant may then be pumped by a water, or coolant, pump (not shown) back to the engine 104 or to another component of the vehicle system. As shown in FIG. 1, coolant may be pumped from the tank 156 to the EGR cooler 134 such that a temperature of exhaust gas flowing through the EGR cooler 134 may be reduced before it enters the intake passage 114. A temperature of the coolant may be measured by a coolant temperature sensor 158 before it enters the engine 104 or the EGR cooler 134. Coolant that passes through the EGR cooler 134 then flows back to the tank 156. In other embodiments, the EGR cooler and the radiator may have separate tanks.

The rail vehicle 106 further includes an engine controller 110 (referred to hereafter as the controller) to control various components related to the rail vehicle 106. As an example, various components of the vehicle system may be coupled to the controller 110 via a communication channel or data bus. In one example, the controller 110 includes a computer control system. The controller 110 may additionally or alternatively include a memory holding non-transitory computer readable storage media (not shown) including code for enabling on-board monitoring and control of rail vehicle operation.

The controller 110 may receive information from a plurality of sensors and may send control signals to a plurality of actuators. The controller 110, while overseeing control and management of the rail vehicle 106, may be configured to receive signals from a variety of engine sensors, as further elaborated herein, in order to determine operating parameters and operating conditions, and correspondingly adjust various engine actuators to control operation of the rail vehicle 106. For example, the engine controller 110 may receive signals from various engine sensors including, but not limited to, engine speed, engine load, intake manifold air pressure, boost pressure, exhaust pressure, ambient pressure, ambient temperature, exhaust temperature, particulate filter temperature, particulate filter back pressure, engine coolant pressure, gas temperature in the EGR cooler, the presence of wear particles, or the like. Correspondingly, the controller 110 may control the rail vehicle 106 by sending commands to various components such as the traction motors 124, the alternator/generator 122, cylinder valves, fuel injectors, a notch throttle, or the like. Other actuators may be coupled to various locations in the rail vehicle.

In one example, the controller 110 may be configured to indicate engine degradation when the presence of metallic wear particles is detected within a flow passage in the engine system. Wear debris, or particles, may be generated within the engine system as engine components degrade. As such, increased production of wear debris may indicate increasing engine degradation. Wear debris may be recirculated through the engine via the EGR system. Recirculation of these particles may result in further engine degradation. Wear particles may be generated from wear of metallic engine components. Thus, metallic particles circulating through the gas flow passages of the engine system may be attracted to a magnetic field produced by a device including a magnet, a group of magnets, or other device such as an induction coil. Such a device may further include a detection circuit electrically coupled to the magnet or detection electrodes. The detection circuit may then communicate with controller 110. By positioning the device, referred to herein as a magnetic particle detector, in a gas flow passage containing at least some exhaust gas during at least some operating conditions, wear particles within the gas flow passage may be detected. The operating conditions may include when the EGR system is enabled.

FIG. 2 shows examples of positions of the device, introduced above, within an engine system 200. In one example, the device is a magnetic particle detector. As engine system 200 is part of vehicle system 100, components in FIG. 2 may be the same as the components described above with respect to FIG. 1. The engine 104 receives intake air for combustion from an intake, such as an intake manifold 215. The intake may be any suitable conduit or conduits through which gases flow to enter the engine. For example, the intake may include the intake manifold 215, the intake passage 114, and the like. The intake passage 114 receives ambient air from an air filter (not shown) that filters air from outside of a vehicle in which the engine 104 may be positioned. Exhaust gas resulting from combustion in the engine 104 is supplied to an exhaust, such as exhaust passage 116. The exhaust may be any suitable conduit through which gases flow from the engine. For example, the exhaust may include an exhaust manifold 217, the exhaust passage 116, and the like.

In the embodiment depicted in FIG. 2, the engine 104 is a V-12 engine having twelve cylinders. In other examples, the engine may be a V-6, V-8, V-10, V-16, I-4, I-6, I-8, opposed 4, or another engine type. As depicted, the engine 104 includes a subset of non-donor cylinders 205, which includes six cylinders that supply exhaust gas exclusively to a non-donor cylinder exhaust manifold 217, and a subset of donor cylinders 207, which includes six cylinders that supply exhaust gas exclusively to a donor cylinder exhaust manifold 219. In other embodiments, the engine may include at least one donor cylinder and at least one non-donor cylinder. For example, the engine may have four donor cylinders and eight non-donor cylinders, or three donor cylinders and nine non-donor cylinders. It should be understood, the engine may have any desired numbers of donor cylinders and non-donor cylinders, with the number of donor cylinders typically lower than the number of non-donor cylinders.

As depicted in FIG. 2, the non-donor cylinders 205 are coupled to the exhaust passage 116 to route exhaust gas from the engine to atmosphere (after it passes through the turbocharger 120, shown in FIG. 1). The donor cylinders 207, which provide EGR, are coupled exclusively to an EGR passage 132 of an EGR system 130 which routes exhaust gas from the donor cylinders 207 to the intake passage 114 of the engine 104, and not to atmosphere. The EGR passage 132 may route exhaust gas to the intake passage 114 either downstream of the turbocharger 120 (high pressure EGR) or upstream of the turbocharger 120 (low pressure EGR). By introducing cooled exhaust gas to the engine 104, the amount of available oxygen for combustion is decreased, thereby reducing combustion flame temperatures and reducing the formation of nitrogen oxides (e.g., $NO_x$).

Exhaust gas flowing from the donor cylinders 207 to the intake passage 114 passes through the EGR cooler 134, as described above for FIG. 1. Additionally, in some embodiments, the EGR system 130 may include an EGR bypass passage 261 that is configured to divert exhaust from the donor cylinders back to the exhaust passage. The EGR bypass passage 261 may be controlled via a valve 263. The valve 263 may be configured with a plurality of restriction points such that a variable amount of exhaust gas is routed to the exhaust passage, in order to provide a variable amount of EGR to the intake.

A magnetic field, produced/applied by a magnetic particle detector 210 (MPD), also referred to as a particle detector, may be positioned at a location within engine system 200. In some embodiments, plural MPD's 210 are positioned in the engine system for respectively producing several magnetic fields at several locations within the engine system. The MPD 210 may communicate electronically with controller 110. In one example, the MPD 210 is positioned in a portion of a gas flow passage such that the device projects through a wall of the gas flow passage and partially into the flow of gas. As shown in FIG. 2, in one example, a first MPD 210 is positioned in intake passage 114, downstream of an outlet of the EGR passage 132 of EGR system 130. In another example, a second MPD 210 is positioned (alternatively or additionally) in the intake manifold 215 at a distal end of a bank of cylinders. Wear debris may flow through the intake manifold 215 and collect at the distal end of the bank of cylinders. As such, a higher concentration of particles may be present in this location, thereby increasing detection of particles with the MPD 210. In yet another example, a third MPD 210 is positioned (alternatively or additionally) in the EGR passage 132, either upstream or downstream of the EGR cooler 134.

The position of the MPD 210 in the EGR passage 132 may depend on a magnetic flux range of the MPD. The magnetic flux range may be a range of temperatures in which the MPD 210 produces a magnetic flux. For example, the MPD 210 may have a lower threshold temperature below which magnetic flux is lost. Similarly, the MPD 210 may have an upper threshold temperature above which magnetic flux is lost. If the MPD 210 is in a flow of gas above the upper threshold temperature, magnetic flux may be lost and particles may either not be attracted to the device or an accurate signal may not be produced by the device. As such, the temperature of the exhaust gas may affect the placement of the MPD 210. In one example, the temperature of the exhaust gas exiting the EGR cooler 134 may be controlled by adjusting cooling of the EGR cooler. In this way, a MPD positioned downstream of the EGR cooler 134 may be maintained within its magnetic flux range. Examples of EGR cooler 134 control in response to an EGR temperature is described further below with regard to FIG. 8.

In embodiments where the MPD 210 comprises one or more magnets (e.g., permanent magnets), depending on placement of the MPD 210 in the engine system 200, the magnets of the MPD may be constructed out of different materials. For example, if the MPD 210 is positioned in a relatively warm location (e.g., upstream of the EGR cooler 134), the magnet(s) may be made out of a material resistant to high temperatures. In another example, if the MPD 210 is positioned downstream from the EGR cooler 134, the magnet may be made out of or coated with a corrosion resistant material. This material or coating may reduce degradation of the magnet due to condensate and/or acid while still being conductive and maintaining a magnetic flux level. In one example, the magnet may be a selenium magnet. In another example, the magnet may be another type of corrosion resistant magnet.

Returning to FIG. 2, in an alternate embodiment, an in-line particle detector 212 may be positioned in-line with the flow of gas. In one example, the in-line particle detector 212 is placed in a side flow passage 214 within the EGR passage 132, downstream of the EGR cooler 134. In another example, the in-line particle detector 212 may be placed in a side flow passage in the intake passage 114 or in the EGR passage 132, upstream of the EGR cooler 134.

As noted above, there may be one or more MPDs positioned in the engine system 200, as shown in FIG. 2. For example, there may only be one MPD 210 located in the EGR passage 132. In another example, there may be one MPD 210 in the EGR passage 132 and one MPD in the intake manifold 215. As such, one or more MPDs 210 may be positioned in one or all of the locations shown in FIG. 2. Additionally, there may be a combination of the MPD(s) 210 and in-line particle detector 212 in the engine system 200.

Figure 3:
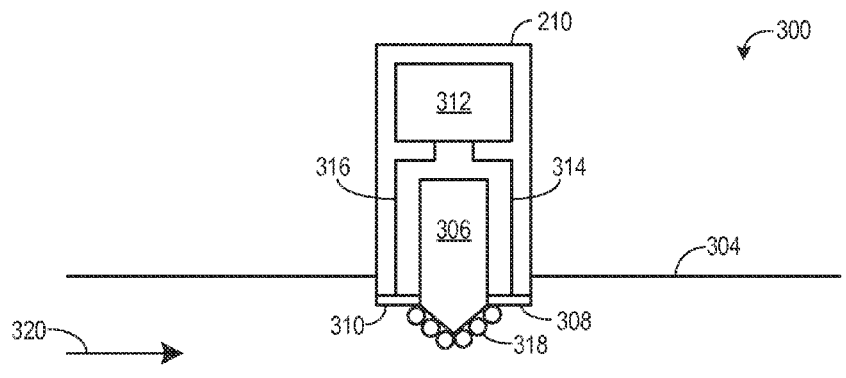
FIGS. 3-5 show configurations of a magnetic particle detector according to an embodiment of the invention.

As discussed above, a magnetic field may be applied with a device positioned in a gas flow passage in an engine. In one example, the device is the MPD 210, shown above in FIG. 2. Applying the magnetic field may include applying the magnetic field with one or more magnetic probes positioned in a portion of a flow of gas. Example configurations of the MPD 210 positioned in a gas flow passage, such as the EGR passage 132, are shown in FIGS. 3-6. FIG. 3 shows a first schematic 300 of a first embodiment of a device configured to generate a magnetic field positioned in a gas flow passage. The device comprises an MPD 210 positioned in a gas flow passage 304. As described above, the gas flow passage 304 may be the intake manifold 215, the EGR passage 132, or the intake passage 114 with a flow of gas 320 which includes at least some exhaust gas. Schematic 300 shows a first example of an MPD 210 in which a central magnetic probe 306 (e.g., magnetic probe between two electrodes), disposed in the gas flow passage, is used to create the magnetic field. Particles 318 in the flow of gas 320 may be attracted to the magnetic probe 306. As described above, particles 318 may be magnetic particles produced from degradation of engine components. Particles 318 may build up or accumulate on the magnetic probe, between a first electrode 308 and a second electrode 310. In response to the buildup of particles 318 between the first electrode 308 and the second electrode 310, an electrical circuit may be closed, thereby producing current. In one example, current flows in a loop down a first electrical conduit 314, to the first electrode 308, to the second electrode 310, and down a second electrical conduit 316, to a detection circuit 312.

The detection circuit 312 may measure the current or signal produced by the electrodes. In one example, the signal may be a current level. When particles 318 buildup and bridge the gap between the first electrode 308 and second electrode 310, the current level may change, indicating a buildup of particles. The controller 110 may receive the signal measured and produced by the detection circuit 312. As such, the controller 110 may indicate engine degradation in response to the signal produced by the MPD 210. An indication may include a warning or indication sent to a vehicle operator. The warning may be one of a first warning indicating the presence of wear debris within the engine system and a second warning indicating engine degradation. In one example, the controller 110 may indicate engine degradation when the signal increases above a first threshold level. In another example, the controller 110 may indicate engine degradation when the buildup of particles increases above a threshold amount of particles. In yet another example, indicating engine degradation may be based on an accumulation rate of particles. For example, the controller 110 may indicate engine degradation in response to an accumulation rate of particles increasing above a threshold rate. As more particles 318 build up between the electrodes, the signal, e.g., current level, may increase. The amount of particles built up between the electrodes, or within the magnetic field, may be determined based on the level of the signal, the spacing between the first electrode 308 and the second electrode 310, and the level of the signal over time. Similarly, the accumulation rate of particles may be determined based on the level of the signal. For example, the rate of increase in the signal may be proportional to the accumulation rate of particles within the magnetic field.

Figure 4:
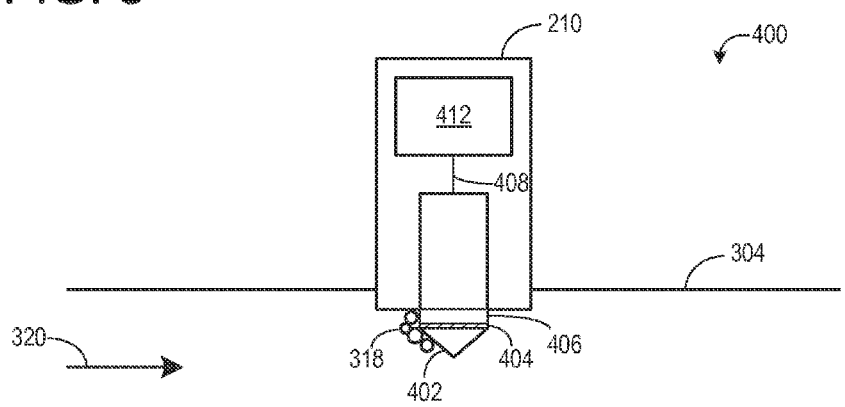

FIG. 4 shows a second schematic 400 of a second embodiment of a device configured to generate a magnetic field positioned in a gas flow passage. The device comprises an MPD 210 positioned in a gas flow passage 304. The MPD 210 shown in schematic 400 includes a magnetic probe 402 (e.g., comprising a magnet) which produces a magnetic field in the gas flow passage 304. Specifically, the magnetic probe is operably coupled with the gas flow passage for establishing the magnetic field in the flow of gas. Particles 318 within the flow of gas 320 may build up between the magnetic probe 402 and an electrode 406, separated by an insulated layer 404. A signal is produced by the particles 318 building up (e.g., accumulating) and bridging the gap between the magnetic probe 402 and the electrode 406. For example, when the particles bridge the gap between the magnetic probe 402 and the electrode 406, current flows from the detection circuit, through an electrical conduit 408, through the magnetic probe 402, through the gap, through the electrode 406, and back to the detection circuit 412 through a second electrical conduit (not shown). The detection circuit 412 then measures the current (e.g., signal) produced by the bridged circuit. As more particles build up between the magnetic probe 402 and the electrode 406, the current level and signal detected by the detection circuit 412 may increase. The detection circuit 412 may function similarly to the detection circuit 312, as described above. As such, the detection circuit 412 may communicate with the controller 110 and signals produced by the MPD 210 may be used by the controller 110 to indicate engine degradation.

Figure 5:
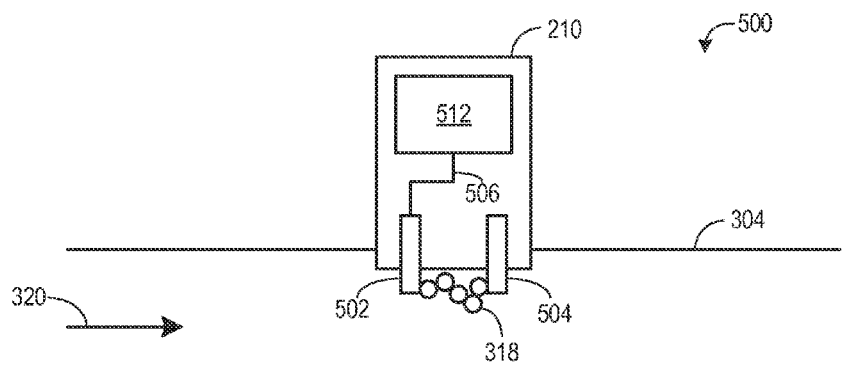

FIG. 5 shows a third schematic 500 of a third embodiment of a device configured to generate a magnetic field positioned in a gas flow passage. The device comprises an MPD 210 positioned in a gas flow passage 304. The MPD 210 shown in schematic 500 includes a first magnetic probe 502 and a second magnetic probe 504, electrically coupled to a detection circuit 512 through electrical conduit 506. Particles 318 traveling in the flow of gas 320 may build up between the first magnetic probe 502 and the second magnetic probe 504. When the gap between the magnetic probes is bridged by the wear particles, a signal is created and measured by the detection circuit 512. The detection circuit 512 may function similarly to the detection circuit 312, as described above. The signal is then tracked over time and used by the controller 110 to indicate engine degradation.

The system of FIGS. 1-5 may provide for an engine system including a flow passage coupled to the engine for passage of a gas flow comprising at least some exhaust gas, and a device (e.g., a magnet) configured to generate a magnetic field positioned in the flow passage. The magnetic field is for attracting particles traveling in the flow passage. A detection circuit may be electrically coupled to the device and/or to an electrode. (For example, the detection circuit may be electrically coupled to the device and to the electrode, or to two electrodes on either side of the device.) The detection circuit is configured to produce a signal responsive to presence of the particles between the magnet and the electrode. In one example, a controller may be configured to indicate engine degradation when the signal from the detection circuit is indicative of the particles being present in an amount above a threshold level or amount. In another example, the controller may be configured to indicate engine degradation when the signal from the detection circuit increases above a threshold level.

In this way, a magnetic field may be applied within a gas flow passage, the gas flow passage including at least some exhaust gas. A signal produced by one or more particles within the flow of gas in the gas flow passage interacting with the magnetic field may then be measured. The signal may include a current produced by the particles bridging a gap between a first surface and a second surface within the gas flow passage, the current flowing from the first surface, across the gap, and to the second surface. In one example, the first and second surface may be first and second electrodes. In another example, the first surface may be a magnetic probe and the second surface may be an electrode. In yet another example, the first and second surface may be a first and second magnetic probe. In response to the signal, a controller may indicate engine degradation. The controller may also determine one or more of an amount of particles within the magnetic field and/or an accumulation rate of particles within the magnetic field, based on a level of the signal. Engine degradation may be further based on the amount of particles and/or the accumulation rate of particles.

Figure 6:
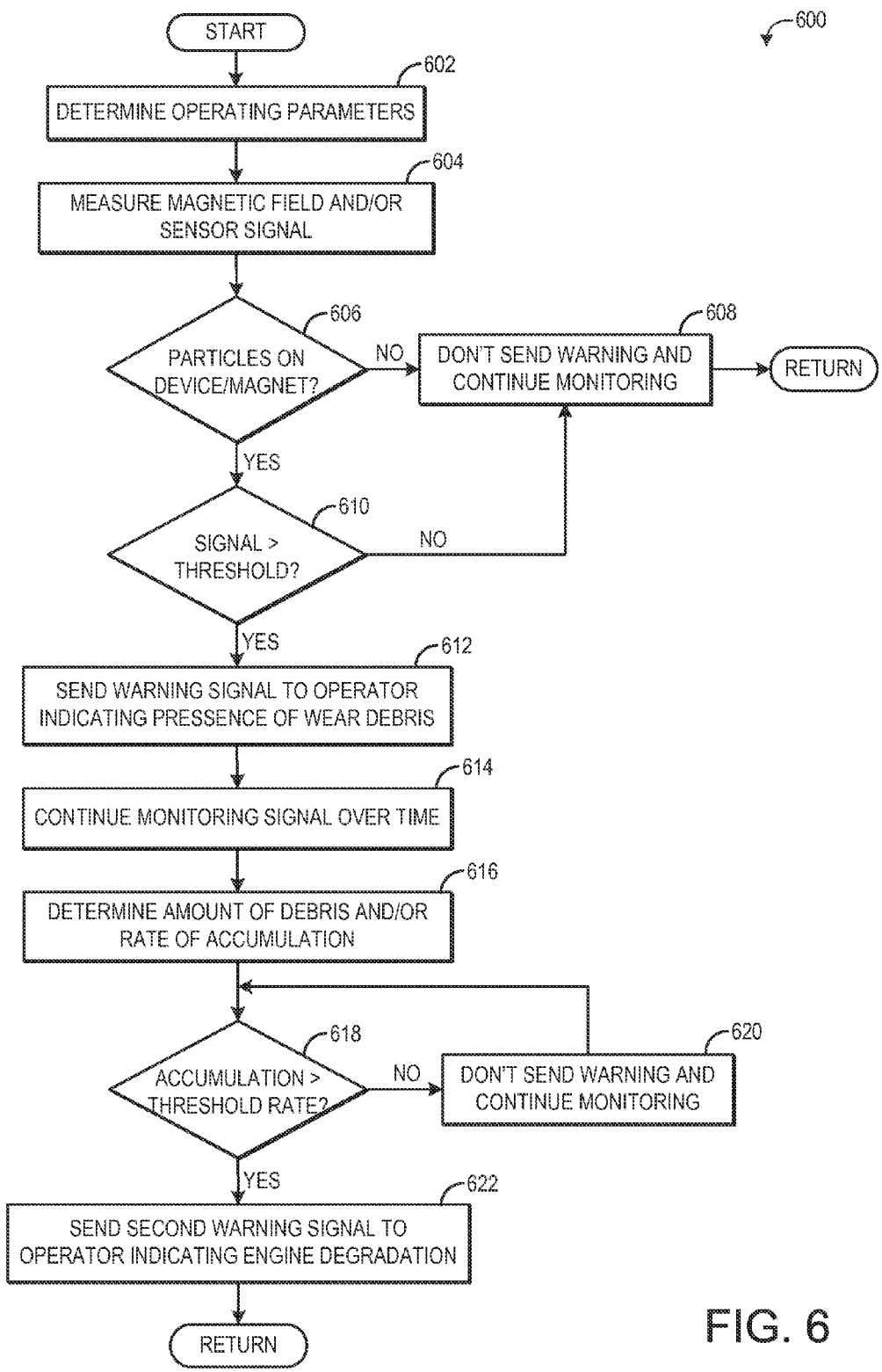
FIG. 6 shows a method for indicating engine degradation in response to a buildup of particles in a magnetic field positioned in a flow of gas according to an embodiment of the invention.

Now turning to FIG. 6, a method 600 is shown for indicating engine degradation in response to an accumulation of particles in a magnetic field positioned in a flow of gas. The method 600 begins at 602 by determining engine operating parameters. Engine operating parameters may include engine speed and load, an EGR flow rate, EGR temperature, and the like. At 604, the method includes measuring the magnetic field and/or the signal from the detection circuit of the MPD. This may include measuring signals from a plurality of MPD devices, as described above with regard to FIGS. 2-5, in different flow passages within the engine system. The signal may include a current level, or a change in current level, as more particles build up on the device.

At 606, the method determines if there are particles within the magnetic field (e.g., particles building up on the MPD). This may include detecting a signal from the MPD, as no signal may be produced if no particles are on the device. If there are not particles on the MPD, no warning signal is sent and the controller continues monitoring the MPD signal at 608. However, if a signal is produced indicating particles on the MPD, the controller determines if the signal is above a first threshold level at 610. If the signal is not above the first threshold level, the method continues monitoring the MPD without sending a warning indicating wear debris at 608. However, if the signal is greater than the first threshold level at 610, the controller may send a warning signal at 612 to the vehicle operator indicating the presence of wear debris (e.g., particles) within the engine system. The first threshold level may be based on an amount of particles that indicate degradation of an engine component. In some embodiments, the method may send a warning after 606 when particles are detected on the MPD. As such, the first threshold level may be any signal produced by the MPD, thereby indicating the presence of wear debris.

At 614, the method includes continuing to monitor the MPD signal over time. At 616, the method determines an amount of debris or particles accumulated on the device. The method at 616 may also include determining a rate of accumulation of the particles. As discussed above, the amount of particles and the rate of accumulation of the particles may be based on the level of the signal detected by the detection circuit. The change in this signal over time, along with the geometry of the MPD, may allow for an estimation of the amount of particles and the accumulation rate of particles. In one example, the MPD includes two magnetic probes, as shown in FIG. 5. In this example, the amount of particles built up between a first magnetic probe and the second magnetic probe may be based on the spacing between the first and second magnetic probes and the level of the signal over time.

At 618, the method determines if the accumulation rate of particles is greater than a threshold rate. The method at 618 may also include determining if the amount of accumulated particles is greater than a threshold amount. If particle accumulation is not greater than one or more of these thresholds, the controller does not send a warning and continues monitoring the MPD signal at 620. However, if the particle accumulation is greater than the threshold rate or threshold amount, the method continues on to 622 where the controller may send a warning signal to the vehicle operator indicating engine degradation. This indication may warn the vehicle operator of engine degradation and request maintenance of the vehicle.

In this way, engine degradation may be indicated in response to a buildup of particles in a magnetic field, the magnetic field positioned in a flow of gas through a gas flow passage of the engine. The buildup of particles may include particles accumulated between a first magnetic probe and a second magnetic probe, particles accumulated between a magnet and an electrode, and/or particles accumulated between a first electrode and a second electrode. The magnetic probes, magnets, and/or electrodes are all disposed within the gas flow passage. Engine degradation may be indicated when the buildup of particles increases above a threshold amount.

Figure 7:
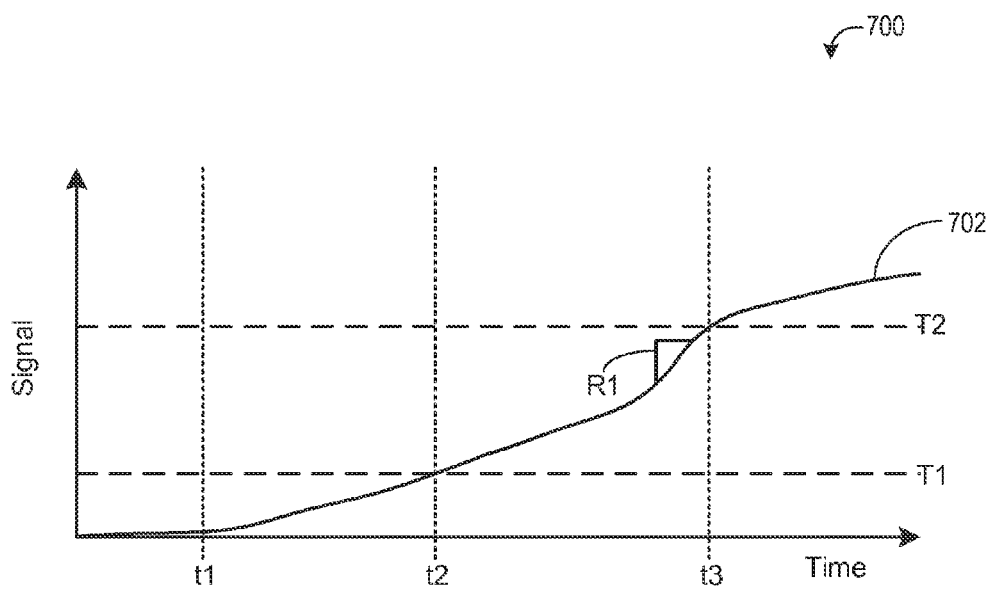
FIG. 7 shows a graph of a signal generated by particles interacting with a magnetic field according to an embodiment of the invention.
Figure 8:
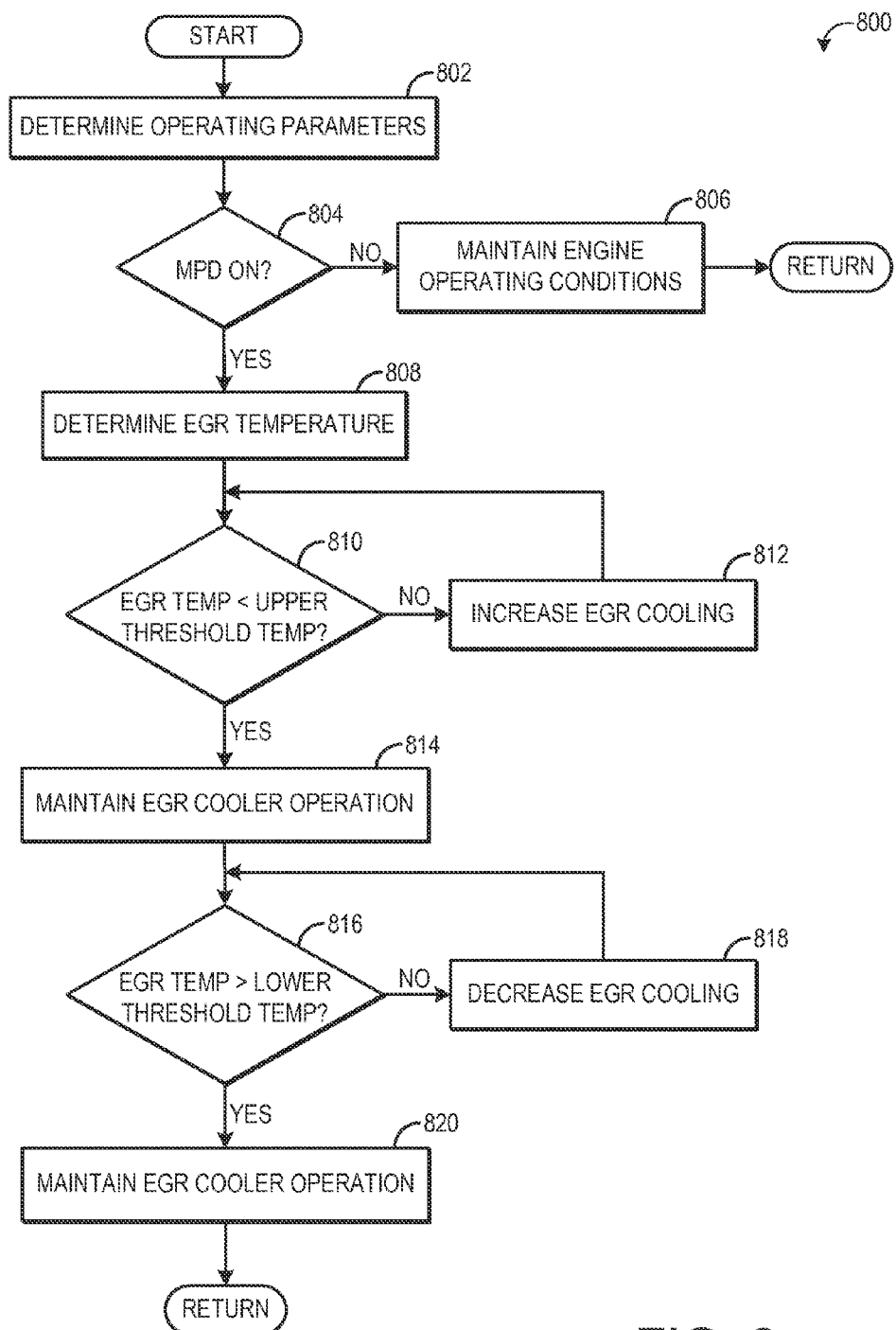
FIG. 8 shows a method for controlling the temperature of a flow of exhaust gas downstream of an exhaust gas recirculation cooler according to an embodiment of the invention.

FIG. 7 shows an example of a graph 700 of a signal generated by the MPD over time. The signal, shown at plot 702, may be a current level or a magnetic flux level. Before time t1, there may be no particles built up on the MPD, thereby not producing a signal. At time t1, the signal increases to a low level in response to particles on the MPD. At time t2, the signal increases over a first threshold level, T1. In response, the controller may send a warning to the vehicle operating indicating wear debris within the engine system. The signal continues to increase between time t2 and time t3 until the signal increases over a second threshold level T2 at time t3. The second threshold level T2 may correspond to a threshold amount of particles or a threshold rate of accumulation of particles. An increase in an accumulation rate R1 of particles is shown just before time t3. In one example, the accumulation rate R1 may be the threshold rate of accumulation of particles. In response to the signal increasing above the second threshold level T2 at time t3, the controller may send an indication to the vehicle operator indicating engine degradation.

As described above with regard to FIG. 2, the magnetic field may be positioned in a portion of an EGR system, downstream of an EGR cooler. The magnetic field may be applied with one or more magnetic probes which may be coated with a temperature resistant material. Additionally, the temperature of the exhaust gas flowing to the MPD downstream of the EGR cooler may be controlled within a temperature range for the magnetic flux range of the magnet. FIG.

8 shows an embodiment of a method 800 for controlling the temperature of the EGR gases based on a temperature range for a MPD.

The method begins at 802 by determining engine operating parameters. Engine operating parameters may include engine speed and load, EGR flow rate, EGR temperature (e.g., temperature of the exhaust gases entering the EGR system upstream and downstream of the EGR cooler), a signal from the MPD, and the like. At 804, the method determines if the MPD is operating or on. This may include detecting an on/off signal from the MPD. If the MPD is not operating, the controller maintains engine operating conditions at 806. However, if the MPD is on at 804, the controller determines the EGR temperature at 808. This may include measuring the temperature of the EGR downstream of the EGR cooler. In an alternate example, the temperature of the EGR exiting the donor exhaust manifold may be used to adjust the EGR cooler operation with a set temperature range. At 810, the method determines if the EGR temperature, downstream of the EGR cooler, is less than an upper threshold temperature. The upper threshold temperature may be a temperature above which magnetic flux of the magnet in the MPD is lost. If the EGR temperature is not less than the upper threshold temperature, the controller may increase cooling of the EGR cooler at 812. Increasing cooling of the EGR cooler may include decreasing a coolant temperature of the EGR cooler coolant and/or decreasing the flow rate of coolant through the EGR cooler. However, if the EGR temperature is less than the upper threshold temperature at 810, the controller maintains EGR cooler operation at 814.

At 816, the method determines if the EGR temperature is greater than a lower threshold temperature. The lower threshold temperature may be a temperature below which magnetic flux of the magnetic probe is lost. If the EGR temperature, downstream of the EGR cooler, is not greater than the lower threshold temperature, the controller may decrease cooling of the EGR cooler at 818. Decreasing cooling of the EGR cooler may include increasing the coolant temperature of the EGR cooler coolant and/or increasing the flow rate of coolant through the EGR cooler. However, if the EGR temperature is greater than the lower threshold temperature at 816, the controller maintains EGR cooler operation at 820. In this way, the temperature of the magnetic probe of the MPD may be controlled within a temperature range for optimal magnetic flux by adjusting operation of the EGR cooler.

Figure 9:
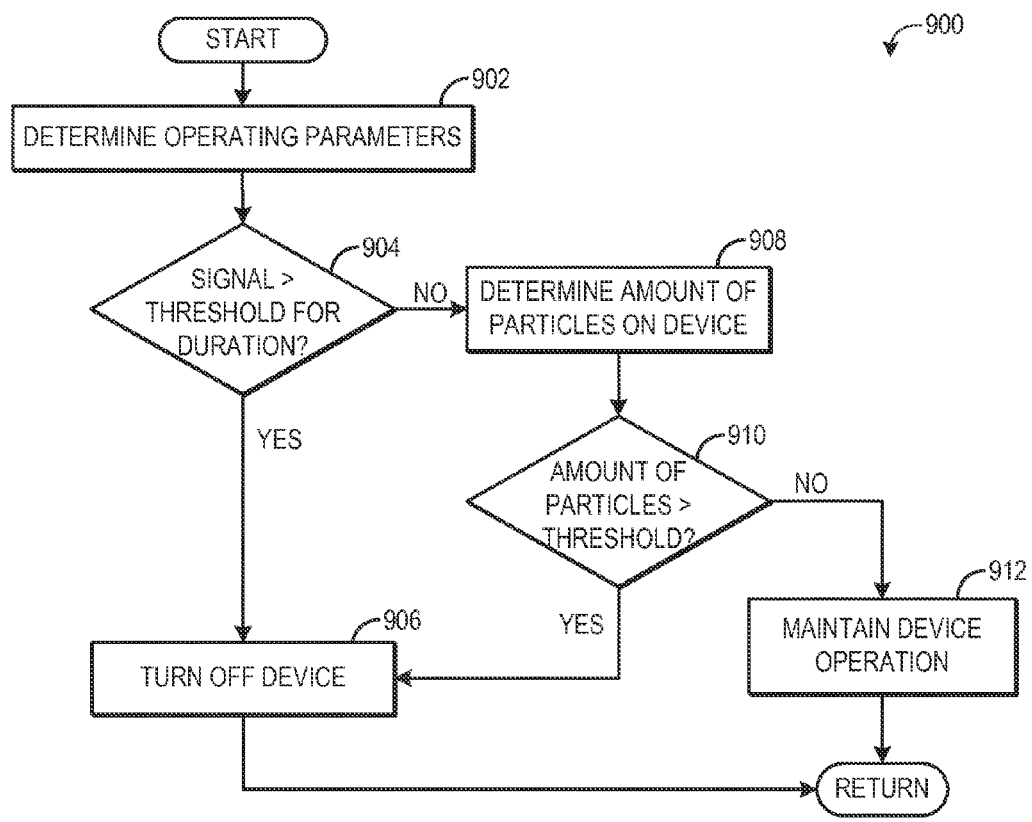
FIG. 9 shows a method for cleaning a particle-fouled magnetic particle detector according to an embodiment of the invention.

After a period of operation, a large amount of particles or wear debris may build up on the MPD. As such, the MPD may undergo a cleaning operation which removes the particles from the surface of the magnetic probes. For example, by de-magnetizing the MPD, or turning off the magnetic flux, particles may be removed from the surface of the MPD and carried downstream with the flow of gas. In one example, cleaning of the MPD may be based on an amount of particles on the device and/or a rate of accumulation of particles. In another example, the cleaning of the MPD may be based on the signal produced by the MPD not changing for a duration. This may indicate that particles can no longer build up on the device and the surface of the magnetic probe or device is fouled with particles. FIG. 9 shows an embodiment of a method 900 for cleaning a particle-fouled MPD.

At 902, the method begins by determining engine operating parameters. Engine operating parameters may include engine speed and load, a signal level of the MPD, EGR flow rate, EGR temperature, and the like. At 904, the method determines if the signal level of the MPD (produced by the detection circuit of the MPD) is greater than a threshold level for a duration. The threshold level may be a signal level that indicates at least some particles have built up on the magnetic probe. If the signal is above the threshold level for a duration, that may indicate that too many particles are built up on the surface of the MPD and may impede flow through the gas flow passage. As such, the controller may turn off the MPD at 906 in response to the signal level greater than a threshold level for a duration. Turning off the device may include reducing the magnetic flux of the MPD or controlling an on/off switch. However, if the signal level is not greater than a threshold level for a duration, the method continues on to 908 to determine the amount of particles on the MPD.

At 910, the method determines if the amount of particles accumulated on the magnetic probes and/or electrodes of the MPD is greater than a second threshold amount. This threshold amount may be different than the threshold amount discussed with regard to FIGS. 6-7. In one example, the second threshold amount may be an amount of particles that covers the surface of the MPD. If the amount of particles on the MPD is not greater than the second threshold amount, the controller maintains MPD device operation at 912. However, if the amount of particles on the MPD is greater than the second threshold amount, the MPD may be turned off or de-magnetized at 906, thereby resulting in the cleaning of the MPD. As a result, function of the MPD may be maintained such that engine degradation may be detected.

In this way, wear particles generated from degradation of an engine component may be detected and used to indicate engine degradation. Particles may be attracted to a magnetic field applied within a gas flow passage of the engine which contains as least some exhaust gas. The magnetic field may be created by one or more magnetic probes of a particle detector or sensor. Interaction of the particles with the magnetic field may produce a signal, the signal increasing with an increasing amount of particles attached to the particle detector. As such, a controller may monitor the signal and alert a vehicle operator as the signal increases, indicating the presence of wear debris and engine degradation.

In embodiments, indicating engine degradation may include automatically controlling the engine and/or a vehicle in which the engine is deployed. For example, the engine may be automatically controlled from its current mode of operation to a lower output mode of operation (e.g., idle). As another example, the engine may be automatically shut off, or automatically shut off after one or more designated criteria are met, such as a vehicle in which the engine is deployed being brought to a stop generally, or brought to a stop at a designated location, such as a siding. In other embodiments, indicating engine degradation may include automatically transmitting a signal to a remote location, such as a centralized database and/or a repair facility, for automatic or other scheduling of repair/maintenance operations. In another example, indicating engine degradation may include automatically controlling the engine to cease EGR at least until one or more designated criteria are met, such as the vehicle being serviced. (For example, the valve 263 could be automatically fully opened, and another valve (not shown) controlling flow into the EGR cooler 134 automatically fully closed.) Temporarily ceasing EGR would at least prevent wear debris from entering the engine block.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    applying a magnetic field within a gas flow passage through which a gas flow passes, the gas flow including at least some exhaust gas; and
    measuring a signal produced by particles in the gas flow interacting with the magnetic field.

2. The method of claim 1, wherein the signal includes a current produced by the particles bridging a gap between a first surface and a second surface within the gas flow passage, the current flowing from the first surface, across the gap, and to the second surface.

3. The method of claim 1, wherein the gas flow passage is part of an engine system, and the method further comprises indicating engine degradation of the engine system in response to the signal.

4. The method of claim 3, further comprising determining one or more of an amount of the particles within the magnetic field or an accumulation rate of the particles within the magnetic field, based on a level of the signal, wherein the indicating engine degradation is further based on the one or more of the amount or the accumulation rate.

5. The method of claim 3, wherein the applying the magnetic field includes applying the magnetic field with one or more magnetic probes attached to the gas flow passage and positioned in at least a portion of the gas flow.

6. The method of claim 5, wherein the signal is produced by the particles accumulating between the one or more magnetic probes and an electrode.

7. The method of claim 5, wherein the signal is produced by the particles accumulating between a first electrode and a second electrode, the first electrode and the second electrode separated by one of the one or more magnetic probes, the one of the one or more magnetic probes centrally located between the first electrode and the second electrode.

8. The method of claim 5, wherein the signal is produced by the particles accumulating between a first magnetic probe and a second magnetic probe of the one or more magnetic probes.

9. The method of claim 8, further comprising determining an amount of the particles accumulated between the first magnetic probe and the second magnetic probe based on a spacing between the first magnetic probe and the second magnetic probe and a level of the signal over time, wherein the indicating engine degradation is further based on the amount of the particles accumulated between the first magnetic probe and the second magnetic probe.

10. The method of claim 1, wherein the gas flow passage includes an exhaust gas recirculation passage of an engine.

11. The method of claim 1, wherein the gas flow passage includes an intake passage of an engine downstream of an outlet of an exhaust gas recirculation system of the engine.

12. The method of claim 1, wherein the gas flow passage includes an intake manifold of an engine at a distal end of a bank of cylinders of the engine.

13. A method, comprising:
    indicating engine degradation of an engine in response to a buildup of particles in a magnetic field, the magnetic field positioned in a flow of gas through a gas flow passage of the engine.

14. The method of claim 13, wherein the buildup of particles includes particles accumulated between a first magnetic probe and a second magnetic probe disposed in the gas flow passage.

15. The method of claim 13, wherein the buildup of particles includes particles accumulated between a magnet and an electrode, wherein the magnet is operably coupled with the gas flow passage for establishing the magnetic field in the flow of gas, and wherein the electrode is disposed in the gas flow passage.

16. The method of claim 13, comprising indicating the engine degradation when the buildup of particles increases above a threshold amount.

17. The method of claim 13, wherein the gas flow passage is part of an exhaust gas recirculation system of the engine and disposed downstream of an exhaust gas recirculation cooler of the engine.

18. The method of claim 17, further comprising applying the magnetic field with one or more magnetic probes, the one or more magnetic probes coated with a temperature resistant material, and cooling the probes.

19. A system, comprising:
    an engine;
    a flow passage coupled to the engine for passage of a gas flow comprising at least some exhaust gas;
    a device configured to generate a magnetic field positioned in the flow passage for attracting particles traveling in the flow passage;
    a detection circuit electrically coupled to at least one of the device or an electrode and configured to produce a signal responsive to presence of the particles between the device and the electrode; and
    a controller configured to indicate engine degradation when the signal from the detection circuit is indicative of the particles being present in an amount above a threshold level.

20. The system of claim 19, wherein the device comprises a magnet.

* * * * *